US010463708B2

(12) United States Patent
Kim

(10) Patent No.: US 10,463,708 B2
(45) Date of Patent: *Nov. 5, 2019

(54) PEPTIDE FOR TREATING OCULAR DISEASES AND COMPOSITION FOR TREATING OCULAR DISEASES COMPRISING SAME

(71) Applicant: GemVax & KAEL CO., LTD., Daejeon (KR)

(72) Inventor: Sang Jae Kim, Seoul (KR)

(73) Assignee: GemVax & KAEL Co., Ltd., Daejeon (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/539,396

(22) PCT Filed: Dec. 22, 2015

(86) PCT No.: PCT/KR2015/014099
§ 371 (c)(1),
(2) Date: Jun. 23, 2017

(87) PCT Pub. No.: WO2016/105086
PCT Pub. Date: Jun. 30, 2016

(65) Prior Publication Data
US 2017/0360870 A1 Dec. 21, 2017

(30) Foreign Application Priority Data
Dec. 23, 2014 (KR) .................. 10-2014-0187531

(51) Int. Cl.
| | |
|---|---|
| *A61K 38/45* | (2006.01) |
| *A61K 38/10* | (2006.01) |
| *A61K 38/02* | (2006.01) |
| *A61K 38/00* | (2006.01) |
| *A61K 38/17* | (2006.01) |
| *A61K 45/06* | (2006.01) |
| *A61K 8/64* | (2006.01) |
| *C07K 7/08* | (2006.01) |
| *C07K 1/10* | (2006.01) |
| *C07K 1/16* | (2006.01) |
| *C07K 1/04* | (2006.01) |
| *C07K 1/06* | (2006.01) |

(52) U.S. Cl.
CPC .............. *A61K 38/02* (2013.01); *A61K 38/10* (2013.01); *A61K 38/17* (2013.01); *C07K 1/045* (2013.01); *C07K 1/061* (2013.01); *C07K 1/10* (2013.01); *C07K 1/16* (2013.01)

(58) Field of Classification Search
CPC ........ A61K 38/45; A61K 38/00; A61K 38/02; A61K 38/10; A61K 38/17; A61K 45/06; A61K 8/64; A61K 31/7068; C07K 14/4703; C07K 1/045; C07K 1/061; C07K 1/10; C07K 1/16; C07K 7/08
USPC ..................... 514/21.4, 13.3, 20.8
See application file for complete search history.

(56) References Cited

U.S. PATENT DOCUMENTS

| | | |
|---|---|---|
| 6,967,211 B2 | 11/2005 | Inoue |
| 7,030,211 B1 | 4/2006 | Gaudernack et al. |
| 7,786,084 B2 | 8/2010 | Benner et al. |
| 7,794,723 B2 * | 9/2010 | Gaudernack ........... A61K 38/45 424/184.1 |
| 8,828,403 B2 | 9/2014 | Filaci et al. |
| 8,933,197 B2 | 1/2015 | Bogin et al. |
| 9,023,987 B2 | 5/2015 | Chung et al. |
| 9,540,419 B2 | 1/2017 | Kim et al. |
| 9,572,858 B2 | 2/2017 | Kim et al. |
| 9,937,240 B2 | 4/2018 | Kim et al. |
| 10,034,922 B2 * | 7/2018 | Kim ............... C12Y 207/07049 |
| 2002/0042401 A1 | 4/2002 | Ferguson et al. |
| 2003/0027769 A1 | 2/2003 | Scialdone et al. |
| 2003/0143228 A1 | 7/2003 | Chen et al. |
| 2006/0106196 A1 | 5/2006 | Gaudernack et al. |
| 2007/0190561 A1 | 8/2007 | Morin et al. |
| 2008/0025986 A1 | 1/2008 | Ozes et al. |
| 2009/0136917 A1 | 5/2009 | Szalay et al. |
| 2009/0186802 A1 | 7/2009 | Alluis et al. |
| 2009/0215852 A1 | 8/2009 | Bascomb et al. |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0053134 A1 | 3/2012 | Jung et al. |

(Continued)

FOREIGN PATENT DOCUMENTS

| | | |
|---|---|---|
| EP | 1020190 A3 | 10/2000 |
| EP | 1093381 B2 | 7/2009 |

(Continued)

OTHER PUBLICATIONS

What is Macular Degeneration from American Macular Degeneration Foundation, pp. 1-6. Accessed Feb. 27, 2019.*
Macular Degeneration Treatments from American Macular Degeneration Foundation, pp. 1-5. Accessed Feb. 27, 2019.*
What Eye Problems Does Graves' Disease Cause from WebMD, pp. 1-7. Accessed Feb. 27, 2019.*
What Causes Dry Eyes? from WebMD, pp. 1-20. Accessed Feb. 27, 2019.*
Albini, A., et al., "Cancer Prevention by Targeting Angiogenesis," Nature reviews Clinical oncology 9(9):498-509, Nature Pub Group (2012).
Auerbach, R., et al., "Angiogenesis Assays: Problems and Pitfalls," Cancer Metastasis Reviews 19(1-2):167-172, Kluwer Academic, Netherlands (2000).

(Continued)

*Primary Examiner* — Julie Ha
(74) *Attorney, Agent, or Firm* — Sterne, Kessler, Goldstein & Fox P.L.L.C.

(57) ABSTRACT

A pharmaceutical composition for preventing or treating ophthalmopathy is described. More particularly, a composition comprising a peptide derived from telomerase and being effective in treating and preventing ophthalmopathy is described. The peptide derived from telomerase, a peptide having a sequence 80% identical to the sequence thereof, or a peptide as a fragment thereof is superiorly effective in treating ophthalmopathy.

15 Claims, 3 Drawing Sheets

Specification includes a Sequence Listing.

(56) References Cited

U.S. PATENT DOCUMENTS

| | | |
|---|---|---|
| 2012/0065124 A1 | 3/2012 | Morishita et al. |
| 2012/0208755 A1 | 8/2012 | Leung |
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim et al. |
| 2015/0307859 A1 | 10/2015 | Kim |
| 2015/0343095 A1 | 12/2015 | Kim et al. |
| 2015/0353903 A1 | 12/2015 | Kim |
| 2016/0002613 A1 | 1/2016 | Kim et al. |
| 2016/0008438 A1 | 1/2016 | Kim |
| 2016/0082089 A1 | 3/2016 | Kim |
| 2016/0120966 A1 | 5/2016 | Kim |
| 2016/0137695 A1 | 5/2016 | Kim |
| 2016/0151512 A1 | 6/2016 | Kim |
| 2016/0250279 A1 | 9/2016 | Kim et al. |
| 2016/0296604 A1 | 10/2016 | Kim |
| 2016/0375091 A1 | 12/2016 | Kim |
| 2017/0028035 A1 | 2/2017 | Kim |
| 2017/0058001 A1 | 3/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0165369 A1 | 6/2017 | Bender |
| 2017/0275603 A1 | 9/2017 | Kim et al. |
| 2017/0360870 A1 | 12/2017 | Kim |
| 2018/0207241 A1 | 7/2018 | Kim |
| 2019/0030137 A1 | 1/2019 | Kim et al. |

FOREIGN PATENT DOCUMENTS

| | | |
|---|---|---|
| EP | 1817337 B1 | 1/2011 |
| EP | 3372613 A1 | 9/2018 |
| JP | 2002522373 A | 7/2002 |
| JP | 2010252810 A | 11/2010 |
| JP | 2012526524 A | 11/2012 |
| JP | 5577472 B2 | 8/2014 |
| KR | 19930001915 A | 2/1993 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060065588 A | 6/2006 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120035150 A | 4/2012 |
| KR | 20120087885 A | 8/2012 |
| KR | 20120121196 A | 11/2012 |
| KR | 20120130996 A | 12/2012 |
| KR | 20120133661 A | 12/2012 |
| KR | 20130004949 A | 1/2013 |
| KR | 20130041896 A | 4/2013 |
| KR | 20140037698 A | 3/2014 |
| WO | WO-0002581 A1 | 1/2000 |
| WO | WO-2010003520 A2 | 1/2010 |
| WO | WO-2010012850 A1 | 2/2010 |
| WO | WO-2010128807 A2 | 11/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167574 A1 | 11/2013 |
| WO | WO-2013169060 A1 | 11/2013 |
| WO | WO 2013169067 A1 | 11/2013 |
| WO | WO-2013169077 A1 | 11/2013 |
| WO | WO-2014010971 A1 | 1/2014 |
| WO | WO-2014012683 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014046983 A1 | 3/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |
| WO | WO-2016105086 A1 | 6/2016 |
| WO | WO-2016137162 A1 | 9/2016 |
| WO | WO-2017078440 A1 | 5/2017 |

OTHER PUBLICATIONS

Berendsen, H.J., "A Glimpse of the Holy Grail?," Science 282(5389):642-643, American Association for the Advancement of Science, United States (1998).

Co-pending Application, U.S. Appl. No. 15/772,928, inventors Kim, S.J., et al., filed Nov. 3, 2016 (Not Published).

Delves, P.J., "Allergic Rhinitis," Merck manual, accessed at http://www.merckmanuals.com/professional/immunology-allergic-disorders/allergic,-autoimmune,-and-other-hypersensitivity-disorders/allergic-rhinitis, accessed on Nov. 2, 2017, pp. 1-6.

Du, C., et al., "Conformational and Topological Requirements of Cell-permeable Peptide Function," The Journal of Peptide Research 51(3):235-243, Munksgaard, Denmark (1998).

Extended European Search Report for Application No. EP14808179, dated May 24, 2017, 24 pages.

Fauce, S.R., et al., "Telomerase-Based Pharmacologic Enhancement of Antiviral function of Human CD8+ T Lymphocytes, "Immunology 181(10):7400-7406, American Association of Immunologists, United States (Nov. 2008).

Fontanes, V., et al., "A cell permeable peptide inhibits Hepatitis C Virus Replication by Sequestering IRES Transacting Factors, " Virology 394(1):82-90, Academic Press, United States (Nov. 2009).

Fried, M.P., "Nonallergic Rhinitis," Merck manual, accessed at http://www.msdmanuals.com/professional/ear,-nose,-and-throat-disorders/nose-and-paranasal-sinus-disorders/nonallergic-rhinitis, accessed on Nov. 2, 2017, pp. 1-3.

International Search Report and Written Opinion for International Application No. PCT/KR2016/012613, Korean Intellectual Property Office, Republic of Korea, dated Feb. 2, 2017, 14 pages.

International Search Report for Application No. PCT/KR2016/007192, dated Sep. 12, 2016, 12 pages.

Jain, R.K., "Barriers to Drug Delivery in Solid Tumors," Scientific American 271(1):58-65, Scientific American, Inc., United States (Jul. 1994).

Kalnins, A., et al., "Sequence of the Lacz Gene of Escherichia coli," The EMBO Journal 2(4):593-597, Wiley Blackwell, England (1983).

Kim, H., et al., "Inhibition of HIV-1 Reactivation by a Telomerase-Derived Peptide in a HSP90-Dependent Manner," Scientific Reports 6: 28896, Nature Publishing Group, England (Jul. 2016).

Kirino, T, "Delayed Neuronal Death in the Gerbil Hippocampus Following Ischemia," Brain Research 239(1):57-69, Amsterdam Elsevier/North-Holland Biomedical Press, Netherlands (May 1982).

Lee, S.A., et al., "A Telomerase-Derived Peptide Regulates Reactive Oxygen Species and Hepatitis C Virus RNA Replication in HCV-Infected Cells via Heat Shock Protein 90, "Biochemical and Biophysical Research Communications 471(1):156-162, Elsevier, United States (Feb. 2016).

(56) References Cited

OTHER PUBLICATIONS

Leem G., et al., Immunotherapy in Pancreatic Cancer; the Road Less Traveled Immunol Disord Immunotherapy, Jun. 26, 2016 (Jun. 26, 2016), p. 1000106, XP055328627, Retrieved from the Internet: (URL:http://www.omicsgroup.org/jjournalsjimmunotherapy-in-pancreatic-cancer-the-road-less-traveled-IDIT-1000104.pdf).
Merck Manual: Respiratory Diseases, Medical Topics, accessed on Nov. 2, 2017, pp. 1-4.
Merck, "Obesity, The Merck Manual Professional Edition," accessed at https://www.merckmanuals.com/professional/nutritional-disorders/obesity-and-the-metabolic-syndrome/obesity, accessed on Oct. 6, 2014, 9 pages.
Middleton, G.W., "A Phase III Randomized Trial of Chemoimmunotherapy Comprising Gemcitabine and Capecitabine with or Without Telomerase Vaccine GV1001 in Patients with Locally Advanced or Metastatic Pancreatic Cancer," Presented at conference ASCO, (Jun. 4, 2013), XP054977010. Retrieved from the Internet: (URL: http://meetinglibrary.asco.orgjcontent/82894?media=vm).
Middleton, G.W., et al., Phase III Randomized Trial of Chemoimmunotherapy Comprising Gemcitabine and Capecitabine with or without Telomerase Vaccine GV1001 in Patients with Locally Advanced or Metastatic Pancreatic Cancer, ASCO Annual Meeting, 31:1-3, (May 31, 2013)-(Jun. 4, 2013), XP055328310.
Middleton, G.W., et al., Poster: Predictive Cytokine Biomarkers for Survival in Patients with Advanced Pancreatic Cancer Randomized to Sequential Chemoimmunotherapy Comprising Gemcitabine and Capecitabine (GemCap) Followed by the Telomerase Vaccine GV1001 Compared to Concurrent Chemoimmunotherapy in the Telovac Phase III tr, ASCO 2014, May 30, 2014 (May 30, 2014)-Jun. 3, 2014 (Jun. 3, 2014), pp. 1-1. XP055328448. Retrieved from the Internet: (URL:http://media4.asco.org/144/8599/93976/93976_poster_pvhr.jpg).
Neoptolemos J.P., et al., "Predictive 1-20 Cytokine Biomarkers for Survival in Patients With Advanced Pancreatic Cancer Randomized to Sequential Chemoimmunotherapy Comprising Gemcitabine and Capecitabine (Gemcap) Followed by the Telomerase Vaccine GV1001 Compared to Concurrent Chemoimmunotherapy in the Telovac Phase III trial, " 2014 ASCO Annual Meeting, May 30, 2014 (May 30, 2014)-Jun. 3, 2014 (Jun. 3, 2014), pp. 1-3.
Ngo. et al., "Computational Complexity, Protein Structure Prediction, and the Levinthal Paradox," in The Protein Folding Problem and Tertiary Structure Prediction, Merz, Jr., K.M., and Le Grand, S.M., eds., pp. 491-494, Birkhauser Boston, United States (1994).
O'Beirne, J., et al., "Generation of Functional CD8+ T Cells by Human Dendritic Cells Expressing Glypican-3 Epitopes," in: Journal of Experimental and Clinical Cancer Research 29:48, BioMed Central, London (May 2010).
Olney, J.W., et al., "Pathological Changes Induced in Cerebrocortical Neurons by Phencyclidine and Related Drugs," Science 244(4910):1360-1362, American Association for the Advancement of Science, United States (Jun. 1989).
Ortega, V.E., "Asthma," Merck manual, accessed at http://www.merckmanuals.com/professional/pulmonary-disorders/asthma-and-related-disorders/asthma, accessed on Nov. 2, 2017, pp. 1-19.
Rosenstein, B.J., "Cystic Fibrosis," Merck manual, accessed at http://www.msdmanuals.com/professional/pediatrics/cystic-fibrosis-cf/cystic-fibrosis, accessed on Nov. 2, 2017, pp. 1-15.
Rudinger, J., "Characteristics of the Amino Acids as Components of a Peptide Hormone Sequence," in Peptide Hormones, Parsons, J.A., ed., University Park Press, United States (1976).
Schwarze, S.R., et al., "In Vivo Protein Transduction: Delivery of a Biologically Active Protein Into the Mouse," Science 285(5433):1569-1572, American Association for the Advancement of Science, United States (1999).
Sigma Genosys, "Designing Custom Peptides," accessed at http://www.sigma-genosys.com/peptide_design.asp, Accessed on Dec. 16, 2004, 2 pages.
Supplemental European Search Report for Application No. EP14808179, dated Jan. 10, 2017, 13 pages.

Varma, N., et al., "Role of hTERT and WT1 Gene Expression in Disease Progression and Imatinib Responsiveness of Patients with BCR-ABL Positive Chronic Myeloid Leukemia," in: Leukemia and Lymphoma 52(4):687-693, Informa Healthcare, London (Apr. 2011).
Voet, D. and Voet, J.G., "Abnormal Hemoglobins," in Biochemistry, 2nd Edition, Chapter 9, pp. 235-241, John Wiley & Sons, Inc., United States (1995).
Written opinion for Application No. PCT/KR2016/007192, dated Sep. 12, 2016, 16 pages.
Altschul, S.F., et al., "Basic Local Alignment Search Tool," Journal of Molecular Biology 215(3):403-410, Elsevier, England (Oct. 1990).
Beer, T.M., et al., "Phase II Study of Weekly Docetaxel in Symptomatic Androgen-independent Prostate Cancer," Annals of Oncology 12(9):1273-1279, Oxford University Press, England (2001).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).
Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Brandenburg, K., et al., "Peptide-based Treatment of Sepsis," Applied Microbiology and Biotechnology 90(3):799-808, Springer International, Germany (2011).
Bruns, A.F., et al., "A Heat-shock Protein Axis Regulates VEGFR2 Proteolysis, Blood Vessel Development and Repair," PloS One 7(11):e48539, Public Library of Science, United States (2012).
Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).
Calderwood, S.K., et al., "Heat Shock Proteins in Cancer: Chaperones of Tumorigenesis," Trends in Biochemical Sciences 31(3):164-172, Elsevier Trends Journals, England (2006).
Cho, Y.J., "GemVax & Kael (082270)," Hana Daetoo Securities, Company Report, Sep. 10, 2012, 9 pages.
Choi, S.G., "Recent Advances in Cancer Cachexia," Journal of Korean Oncology Nursing 11(1):20-25 (2011).
ClinicalTrials.gov, "Adjuvant Leuprolide with or without Docetaxel in High Risk Prostate Cancer After Radial Prostatectomy," Identifier NCT00283062, first received on Jan. 26, 2006, accessed at https://clinicaltrials.gov/ct2/show/study/NCT00283062, last accessed on May 12, 2017, 7 pages.
ClinicalTrials.gov, "Gemcitabine, Capecitabine, and Telomerase Peptide Vaccine GV1001 in Treating Patients With Locally Advanced and Metastatic Pancreatic Cancer," Identifier NCT00425360, accessed at https://clinicaltrials.gov/archive/NCT00425360/2007_01_22, last accessed on Apr. 7, 2017, 4 pages.
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).
Zhou, J., et al., "PI3K/Akt is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).
Co-pending U.S. Appl. No. 15/553,689, inventor Kim, S.J., et al., I.A. filed Feb. 18, 2016 (Not Published).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
De Araujo, J.G., et al., "The Potential Use of Melatonin for Preventing Cisplatin Ototoxicity: An Insight for a Clinical Approach," Advances in Otolaryngology 2014:8 pages, Hindawi Publishing Corporation (2014).

(56) References Cited

OTHER PUBLICATIONS

Dementia from Merck Manual, accessed on Jul. 29. 2009, pp. 1-17.
Dempsey, N.C., et al., "Differential Heat Shock Protein Localization in Chronic Lymphocytic Leukemia," Journal of Leukocyte Biology 87(3):467-476, Society for Leukocyte Biology, United States (2010).
Dinarello, C.A., "Interleukin-1 in the Pathogenesis and Treatment of Inflammatory Diseases," Blood117(14):3720-3732, American Society of Hematology, United States (2011).
Du, R., et al., "HIF1alpha Induces the Recruitment of Bone Marrow-derived Vascular Modulatory Cells to Regulate Tumor Angiogenesis and Invasion," Cancer Cell 13(3):206-220, Cell Press, United States (2008).
Eisenegger, C., et al., "The Role of Testosterone in Social Interaction," Trends in Cognitive Sciences 15(6):263-271, Elsevier Science, England (2011).
Engineer, D.R. and Garcia, J.M., "Leptin in Anorexia and Cachexia Syndrome," International Journal of Peptides 2012:Article ID 287457, Hindawi Publishing Corporation, United States (2012).
"Seoul National University Bundang Hospital excited because of '000'," Clinical trials of Dream Anticancer Drug without side effects with Kael & GemVax, 4 pages, Apr. 22, 2013.
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).
Ferrarini, M., et al., "Unusual Expression and Localization of Heat-shock Proteins in Human Tumor Cells," International Journal of Cancer51(4):613-619, Wiley-Liss, United States (1992).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fujii, H., et al., "Telomerase Insufficiency in Rheumatoid Arthritis," Proceedings of the National Academy of Sciences USA 106(11):4360-4365, National Academy of Sciences, United States (2009).
Garcia-Carbonero, R., et al., "Inhibition of HSP90 Molecular Chaperones: Moving Into the Clinic," The Lancet Oncology 14(9):e358-e369, Lancet Publishing Group, England (2013).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Guo, R.F., et al., "Regulatory Effects of Eotaxin on Acute Lung Inflammatory Injury," Journal of Immunology 166(8):5208-5218, American Association of Immunologists, United States (2001).
Heitz, F., et al., "Twenty Years of Cell-Penetrating Peptides: From Molecular Mechanisms to Therapeutics," British Journal of Pharmacology 157(2):195-206, Wiley, England (2009).
Heldin, C.H., et al., "TGF-Beta Signalling from Cell Membrane to Nucleus through SMAD Proteins," Nature 390(6659):465-471, Nature Publishing Group, England (1997).
Henry, J.Y., et al., "Lenalidomide Enhances the Anti-prostate Cancer Activity of Docetaxel in vitro and in vivo," The Prostate 72(8):856-867, Wiley-Liss, United States (2012).
Hse, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor and Francis, United States (2012).
International Preliminary Report on Patentability and Written Opinion for International Application No. PCT/KR2015/014099, The International Bureau of WIPO, dated Jun. 27, 2017, 16 pages.
International Preliminary Report on Patentability and Written Opinion for International Application No. PCT/KR2016/001646, Korean Intellectual Property Office, Republic of Korea, dated May 20, 2016, 13 pages.
International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Preliminary Report on Patentability for International Application No. PCT/KR2014/011280, The International Bureau of WIPO, Geneva, Switzerland, dated May 24, 2016, 15 pages.
International Preliminary Report on Patentability for International Application No. PCT/EP2013/059460, International Bureau of WIPO, Switzerland, dated Nov. 11, 2014, 5 pages.
NPL52 International Preliminary Report on Patentability for International Application No. PCT/KR2013/004145, The International Bureau of WIPO, Switzerland, dated Nov. 11, 2014,14 pages.
International Preliminary Report on Patentability for International Application No. PCT/KR2013/004176, The International Bureau of WIPO, Switzerland, dated Nov. 11, 2014,14 pages.
International Preliminary Report on Patentability for International Application No. PCT/KR2013/006218, The International Bureau of WIPO, Switzerland, dated Jan. 13, 2015, 27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Application No. PCT/KR2014/010035, Korean Intellectual Property Office, Republic of Korea, dated Apr. 26, 2016, 13 pages.
International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/KR2014/011280, Korean Intellectual Property Office, Republic of Korea, dated Feb. 11, 2015, 12 pages.

(56) References Cited

OTHER PUBLICATIONS

International Search Report for International Application No. PCT/KR2015/014099, Korean Intellectual Property Office, Republic of Korea, dated May 4, 2016, 8 pages.
International Search Report for International Application No. PCT/KR2016/001646, Korean Intellectual Property Office, Republic of Korea, dated May 20, 2016, 8 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2014/004752, Korean Intellectual Property Office, Republic of Korea, dated Jan. 16, 2015, 10 pages.
International Search Report for International Application No. PCT/KR20141005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Application No. PCT/KR2014/010035, Korean Intellectual Property Office, Republic of Korea, dated Feb. 2, 2015, 8 pages.
International Search Report for International Application No. PCT/KR2015/003642, Korean Intellectual Property Office, Republic of Korea, dated Jul. 3, 2015, 8 pages.
International Search Report for International Patent Application No. PCT/KR2013/004156, Korean Intellectual Property Office, Republic of Korea, dated Aug. 14, 2013, 10 pages.
International Search Report for International Application No. PCT/KR2014/012502, Korean Intellectual Property Office, Republic of Korea, dated Mar. 11, 2015, 10 pages.
International Search Report for International Application No. PCT/KR2013/008459, Korean Intellectual Property Office, Republic of Korea, dated Dec. 23, 2013, 8 pages.
International Preliminary Report on Patentability for International Application No. PCT/KR2014/012502, The International Bureau of WIPO, Geneva, Switzerland, dated Jun. 21, 2016, 22 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Jemal, A., et al., "Cancer Statistics, 2008," CA: A Cancer Journal for Clinicians 58(2):71-96, Wiley, United States (2008).
Kawasaki, H., et al., "Detection and Evaluation of Activation of Various Cancer Antigenic Peptide-specific CTLs in Mature Dendritic Cells Used for Dendritic Cell Therapy," The 21st International Congress of Personalized Medicine, Conference Program and Abstracts, Personalized Medicine Universe (Japanese edition) 4(Supplement 2): 2 pages, Oct. 17, 2015.
Kern, K.A. and Norton, J.A., "Cancer Cachexia," Journal of Parenteral and Enteral Nutrition 12(3):286-298, Sage Publications, United States (1988).
Kim, B.H., "Presbycusis: Review for its Environmental Risk Factors," Korean Journal of Otorhinolaryngology-Head and Neck Surgery 49(10):962-967, Korean Society of Otolaryngology-Head and Neck Surgery, Korea (2006).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).
Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Kyte, J.A., "Cancer Vaccination with Telomerase Peptide GV1001," Expert Opinion on Investigational Drugs 18(5):687-694, Taylor & Francis, England (2009).
Kyte, J.A., et al., "Telomerase Peptide Vaccination Combined with Temozolomide: A Clinical Trial in Stage IV Melanoma Patients," Clinical Cancer Research 17(13):4568-4580, American Association of Cancer Research, United States (2011).
Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (Jun. 2015).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Mandal, A., "Types of Fibrosis," Retrieved from the internet on Jul. 3, 2014, pp. 1-3.
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Massague, J., "Tgf-Beta Signal Transduction," Annual Review of Biochemistry 67:753-791, Annual Reviews, United States (1998).
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
Middleton, G., et al., "Gemcitabine and Capecitabine With or Without Telomerase Peptide Vaccine GV1001 in Patients With Locally Advanced or Metastatic Pancreatic Cancer (TeloVac): an Open-label, Randomised, Phase 3 Trial," The Lancet. Oncology 15(8):829-840, Lancet Pub. Group, England (2014).

(56) References Cited

OTHER PUBLICATIONS

Modica-Napolitano, J.S. and Singh, K.K., "Mitochondria as Targets for Detection and Treatment of Cancer," Expert Reviews in Molecular Medicine 4(9):1-19, Cambridge University Press, England (2002).
Morano, K.A., "New Tricks for an Old Dog: the Evolving World of Hsp70," Annals of the New York Academy of Sciences 1113:1-14, Blackwell, United States (2007).
Morishita, M., and Peppas, N.A., "Is the Oral Route Possible for Peptide and Protein Drug Delivery?," Drug Discovery Today 11(19-20):905-910, Elsevier Science Ltd., England (2006).
Murphy, M.E., "The Hsp70 Family and Cancer," Carcinogenesis 34(6):1181-1188, IRL Press, England (2013).
Myers, L.K., et al., "Collagen-Induced Arthritis, an Animal Model of Autoimmunity," Life Sciences 61(19):1861-1878, Elsevier, Netherlands (1997).
Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).
National Center for Biotechnology Information, "Hormones," MeSH Database, Bethesda, accessed at http://www.ncbi.nlm.nih.gov/mesh/68006728, accessed on May 8, 2017, 3 pages.
National Horizon Scanning Centre News on Emerging Technologies in Healthcare, GV1001 for Advanced and/or Metastatic Pancreatic Cancer, Published Apr. 2008.
National Institute of Diabetes and Digestive and Kidney Diseases, "Prostate Enlargement: Benign Prostatic Hyperplasia," accessed at https://www.niddk.nih.gov/health-information/urologic-diseases/prostate-problems/prostate-eniargement-benign-prostatic-hyperplasia, accessed Sep. 2014, 14 pages.
Nawroth, I., et al., "Intraperitoneal Administration of Chitosan/DsiRNA Nanoparticles Targeting TNFα Prevents Radiation-induced Fibrosis," Radiotherapy and Oncology 97(1):143-148, Elsevier Scientific Publishers, Ireland (2010).
NCBI, Reference Sequence: XP_003776612.1 (Jul. 17, 2012).
Novina, C.D. And Sharp, P.A., "The RNAi Revolution," Nature 430(6996):161-164, Nature Publishing Group, England (2004).
Oh, H., et al., "Telomerase Reverse Transcriptase Promotes Cardiac Muscle Cell Proliferation, Hypertrophy, and Survival," Proceedings of the National Academy of Sciences USA 98(18): 10308-10313, National Academy of Sciences, United States (2001).
Pearson, W.R. and Lipman, D.J., "Improved Tools for Biological Sequence Comparison," Proceedings of the National Academy of Sciences of the United States of America 85(8):2444-2448, National Academy of Sciences, United States (1988).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeting HSP70: the Second Potentially Druggable Heat Shock Protein and Molecular Chaperone?," Cell Cycle 9(8):1542-1550, Taylor & Francis, United States (2010).
Priya, S.G., et al., "Skin Tissue Engineering for Tissue Repair and Regeneration," Tissue Engineering. Part B, Reviews 14(1):105-118, Mary Ann Liebert, Inc., United States (2008).
Rana, T.M., "Illuminating the Silence: Understanding the Structure and Function of Small RNAs," Nature Reviews. Molecular Cell Biology 8(1):23-36, Nature Publishing Group, England (2007).
Rheumatoid Arthritis from Merck Manual, accessed on Apr. 21, 2016, pp. 1-18.
Rosenbloom, J., et al., "Strategies for Anti-fibrotic Therapies," Biochirnica et Biophysica Acta 1832(7):1088-1103, Elsevier Pub. Co., Netherlands (2013).
Roubenoff, R., et al., "Adjuvant Arthritis as a Model of Inflammatory Cachexia," Arthritis and Rheumatism 40(3):534-539, Wiley-Blackwell, United States (1997).
Rowe-Rendleman, C. and Glickman, R.D., "Possible therapy for age-related macular degeneration using human telomerase," Brain Research Bulletin 62(6):549-553, Elsevier Science Inc., United States (2004).
Sasada, A., et al., "A Case of Elderly Patient With Lung Cancer Efficiently Treated With Dendritic Cell Immunotherapy" The 20th International Congress of Personalized Medicine, Conference Program and Abstracts, Personalized Medicine Universe (Japanese edition) 4(Supplement 1): 2 pages, May 24, 2015.
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Schenk, D., et al., "Immunization with Amyloid-beta Attenuates Alzheimer-disease-like Pathology in the PDAPP Mouse," Nature 400(6740):173-177, Nature Publishing Group, England (1999).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Seo, J.S., et al., "T Cell Lymphoma in Transgenic Mice Expressing the Human Hsp70 Gene," Biochemical and Biophysical Research Communications 218(2):582-587, Elsevier, United States (1996).
Shaw, V,E., et al., "Current Status of GV1001 and Other Telomerase Vaccination Strategies in the Treatment of Cancer," Expert Review of Vaccines 9(9):1007-1016, Taylor & Francis, England (2010).
Shay, J.W., and Wright, W.E., "Telomerase Therapeutics for Cancer: Challenges and New Directions," Nature Reviews. Drug Discovery 5(7):577-584, Nature Publishing Group, England (2006).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (Jul. 1988).
Smith, T.F. and Waterman, M.S., "Comparison of Biosequences," Advances in Applied Mathematics 2(4):482-489, Academic Press, Inc., United States (Dec. 1981).
Song, J., et al., "Characterization and Fate of Telomerase-Expressing Epithelia during Kidney Repair," Journal of the American Society of Nephrology 22(12):2256-2265, American Society of Nephrology, United States (2011).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.
Stevenson, C.L., "Advances in Peptide Pharmaceuticals," Current Pharmaceutical Biotechnology 10(1):122-137, Bentham Science Publishers, United Arab Emirates (2009).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al., "Clustal W: Improving the Sensitivity of Progressive Multiple Sequence Alignment through Sequence Weighting, Position-specific Gap Penalties and Weight Matrix Choice," Nucleic Acids Research 22(22):4673-4680, Oxford University Press, England (Nov. 1994).
Tisdale, M.J., "Catabolic Mediators of Cancer Cachexia," Current Opinion in Supportive and Palliative Care, 2(4):256-261, Lippincott Williams & Wilkins, United States (2008).
Tisdale, M.J., "Mechanisms of Cancer Cachexia," Physiological Reviews 89(2):381-410, American Physiological Society, United States (2009).
Tomari Y. and Zamore, P.D., "Perspective: Machines for RNAi," Genes and Development 19(5):517-529, Cold Spring Harbor Laboratory Press, United States (2005).

(56) References Cited

OTHER PUBLICATIONS

Uehara, Y., "Natural Product Origins of Hsp90 Inhibitors," Current Cancer Drug Targets 3(5):325-330, Bentham Science Publishers, Netherlands (2003).
Van Coppenolle, F., et al., "Effects of Hyperprolactinernia on Rat Prostate Growth: Evidence of Androgeno-dependence," American Journal of Physiology. Endocrinology and Metabolism 280(1):E120-E129, American Physiological Society, United States (2001).
Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Vennela, B., et al., "Current and Future Strategies for Therapy of Pancreatic Cancer," International Journal of Research in Pharmacy and Medicine 2(3):728-740 (2012).
Volloch, V.Z. and Sherman, M.Y., "Oncogenic Potential of Hsp72," Oncogene 18(24):3648-3651, Nature Publishing Group, England (1999).
Walsmith, J. and Roubenoff, R., "Cachexia in Rheumatoid Arthritis," International Journal of Cardiology 85(1):89-99, Elsevier, Netherlands (2002).
Wang, W., et al., "Alleviating the lschemia-Reperfusion Injury of Donor Liver by Transfection of Exogenous hTERT Genes," Transplantation Proceedings 41(5):1499-1503, Elsevier Science, United States (2009).
Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).
Written Opinion for International Application No. PCT/KR2014/011280, Korean Intellectual Property Office, Republic of Korea, dated Feb. 11, 2015, 14 pages.
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2014/004752, Korean Intellectual Property Office, Republic of Korea, dated Jan. 16, 2015, 21 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Application No. PCT/KR2014/010035, Korean Intellectual Property Office, Republic of Korea, dated Feb. 2, 2015, 11 pages.
Written Opinion for International Application No. PCT/KR2015/003642, Korean Intellectual Property Office, Republic of Korea, dated Jul. 3, 2015, 16 pages.
Written Opinion for International Application No. PCT/KR2013/008459, Korean Intellectual Property Office, Republic of Korea, dated Dec. 23, 2013, 9 pages.
Written Opinion for International Patent Application No. PCT/KR2013/004156, Korean Intellectual Property Office, Republic of Korea, dated Aug. 14, 2013, 13 pages.
Written Opinion for International Application No. PCT/KR2014/003425, Korean Intellectual Property Office, Republic of Korea, dated Jul. 21, 2014, 13 pages.
Written Opinion for International Application No. PCT/KR2014/012502, Korean Intellectual Property Office, Republic of Korea, dated Mar. 11, 2015, 20 pages.
Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Yeh, C.H., et al., "Clinical Correlation of Circulating Heat Shock Protein 70 in AcuteLeukemia," Leukemia Research 34(5):605-609, Pergamon Press, England (2010).
Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Petrylak D.P., "The Treatment of Hormone-Refractory Prostate Cancer: Docetaxel and Beyond," Reviews in Urology 8 (Suppl 2): S48-S55, United States (2006).
Hey, Y.Y and O'Neill, H.C., "Murine spleen contains a diversity of myeloid and dendritic cells distinct in antigen presenting function," Journal of Cellular and Molecular Medicine, 16(11):2611-2619, Wiley-Blackwell, England (Nov. 2012).
Tarantino, G., et al. "Spleen: a New Role for an Old Player?," World Journal of Gastroenterology, 17(33):3776-3784, Baishideng Publishing Group, United States (Sep. 2011).
Shay, J.W., and Keith, W.N., "Targeting Telomerase for Cancer Therapeutics," in: British Journal of Cancer 98(4):677-683, Nature Publishing Group on behalf of Cancer Research UK (2008).

* cited by examiner

PEPTIDE FOR TREATING OCULAR DISEASES AND COMPOSITION FOR TREATING OCULAR DISEASES COMPRISING SAME

CROSS-REFERENCE TO RELATED APPLICATIONS

This application is the U.S. national phase of PCT/KR2015/014099, filed Dec. 22, 2015, which claims foreign priority to KR 10-2014-0187531, flied Dec. 22, 2014, which are hereby incorporated by reference herein in its entirety.

REFERENCE TO SEQUENCE LISTING SUBMITTED ELECTRONICALLY VIA EFS-WED

The content of the electronically submitted sequence listing (Name: 2473_0980000_SeqLiSting.txt 10,347 bytes; and Date of Creation; Jun. 22, 2017) was originally submitted in the International Application No. PCT/KR9015/014099 and is incorporated herein by reference in its entirety.

BACKGROUND OF THE INVENTION

Field of the Invention

The present invention relates to a peptide having a therapeutic effect on ophthalmopathy, and a pharmaceutical composition including the same. More particularly, the present invention relates to a peptide having a therapeutic effect on ophthalmopathy as a peptide derived from telomerase, and pharmaceutical composition including the same for treating ocular diseases.

Background Art

Age-related macular degeneration is the most serious disease that causes blindness in the elderly over the age of 65 in the West, and has been reported to be an important factor causing amblyopia and blindness due to aging even in the Asian countries. As the population has aged in recent years, the onset of age-related macular degeneration becomes one of diseases having the highest social burden on treatment costs.

Choroidal neovascularization (CNV) shows distinctive signs of wet age-related macular degeneration as neovascularization originating from the choroid, which is caused in a space beneath the retina or retinal epithelium due to the rupture of Bruch's membranes.

No pathophysiology of age-related macular degeneration has been completely found so far. However, various clinical trials and studies show that a vascular endothelial growth factor (VEGF) plays an important role in the onset of choroidal neovascularization. As a result, although laser treatment, photodynamic therapy, and the like have been used in the prior art to treat age-related macular degeneration, current anti-vascular endothelial growth factor antibody (anti-VEGF antibody) injection has established itself as primary therapy, and anti-VEGF antibody drugs such as ranibizumab, bevacizumab, aflibercept, and the like have been used all over the world as a therapeutic agent to treat wet age-related macular degeneration.

Although current primary therapeutic agents for wet age-related macular degeneration are found to be effective for most patients, no one can deny that they have various limitations as injection therapy in which a therapeutic agent is directly intravitreally administered. Because they have a limit on a time at which their medicinal effect last in the eyes, patients should receive repeated injection treatments at intervals of as little as one month. It is a big burden on both practitioners and patients for the patients to receive the endless injection treatments due to the nature of continuously recurring choroidal neovascularization even when the choroidal neovascularization is clinically improved.

Another problem is that the onset of geographic retinal atrophy increases when an anti-VEGF antibody injection is repeatedly administered. Also, the repeated intravitreal injection treatments have their limits since they have a risk of various ocular adverse events including slight side effects such as subconjunctival ecchymosis, etc., and sever complications such as endophthalmitis, retinal detachment, increased intraocular pressure, etc.

Also, the social costs associated with expensive antibody injections and injection therapy, the degradation in quality of life of a patient caused by frequent hospital visits, and the practitioners' excessively increased workload are also problems.

However, another big problem is, first of all, that there is a group of patients having no response to the anti-VEGF antibody injection. In the patient group, even when an anti-VEGF antibody is repeatedly injected to some patients, the activity of choroidal neovascularization is not reduced at all from the beginning, and some patients have no improved vision. Some other patients have a response to the anti-VEGF antibody injection at the beginning, but show tachyphylaxis in which the medicinal effect drops. This indirectly suggests that other factors other than the vascular endothelial growth factor are associated with the pathophysiology of choroidal neovascularization. In effect, it is reported that oxidative stress caused by reactive oxygen species (ROS), inflammatory response in tissues, or the like is associated with the onset and growth of choroidal neovascularization. Accordingly, antioxidants, free radical scavengers, steroids, and the like have been developed as therapeutic agents for treating wet age-related macular degeneration, but still play a subsidiary role in the anti-VEGF antibody injection.

SUMMARY OF THE INVENTION

Technical Problem

Accordingly, this research proves the validity and safety of telomerase-derived peptides in an animal model of choroidal neovascularization in which the inflammatory response in tissues is a part of the important pathophysiology. An inhibitory effect of the telomerase-derived peptides on choroidal neovascularization is proven through this experiment. Because such peptides are drugs having a different mechanism than the conventional anti-VEGF antibody injections, the peptides may serve as another therapeutic weapon in treating the wet age-related macular degeneration in the future, and are also expected to be applicable to various inflammatory diseases other than the ocular diseases to provide a big help in effectively treating an inflammation without any side effects.

Technical Solution

To achieve the objects of the present invention, according to one aspect of the present invention, there is provided a composition for treating and preventing ophthalmopathy, which includes a peptide selected from a peptide including an amino acid sequence set forth in SEQ ID NO: 1, a peptide having a sequence homology of 80% or more with the amino acid sequence, or a fragment thereof.

In the composition according to one aspect of the present invention, the fragment may be a fragment consisting of three or more amino acids.

In the composition according to one aspect of the present invention, the ophthalmopathy may include one or more selected from the group consisting of diabetic retinopathy, retinopathy of prematurity, corneal graft rejection, neovascular glaucoma, rubeosis, proliferative retinopathy, dry eye syndrome, and macular degeneration.

In the composition according to one aspect of the present invention, the ophthalmopathy may be age-related ophthalmopathy.

In the composition according to one aspect of the present invention, the peptide may reduce the activity of a vascular endothelial growth factor (VEGF).

In the composition according to one aspect of the present invention, the peptide may inhibit choroidal neovascularization.

According to another aspect of the present invention, there is provided a composition inhibiting choroidal neovascularization, which includes a peptide selected from a peptide including an amino acid sequence set forth in SEQ ID NO: 1, a peptide having a sequence homology of 80% or more with the amino acid sequence, or a fragment thereof.

In the composition according to another aspect of the present invention, the composition may be a pharmaceutical composition further including a pharmaceutically acceptable excipient and additives.

In the composition according to another aspect of the present invention, the composition may be a food composition.

According to still another aspect of the present invention, there is provided a method of treating and preventing ophthalmopathy, which includes administering the composition for treating and preventing ophthalmopathy to a target.

According to yet another aspect of the present invention, there is provided a kit for treating and preventing ophthalmopathy, which includes the composition for treating and preventing ophthalmopathy, and a manual.

In the kit according to yet another aspect of the present invention, the manual may contain contents regarding the administration of the composition for treating and preventing ophthalmopathy.

According to yet another aspect of the present invention, there is provided a use of the peptide in ophthalmopathy to prepare the composition for treating and preventing ophthalmopathy. Here, the peptide may be selected from a peptide containing an amino acid sequence set forth in SEQ ID NO: 1, a peptide having a sequence homology of 80% or more with the amino acid sequence, or a fragment thereof.

Advantageous Effects of the Invention

According to one exemplary embodiment of the present invention, a composition capable of effectively treating ophthalmopathy can be provided. Therefore, the composition according to one exemplary embodiment of the present invention can be applied to treatment and prevention of ophthalmopathy, and can be particularly used to treat ocular diseases caused by choroidal neovascularization.

Also, the peptide according to one exemplary embodiment of the present invention selected from a peptide containing an amino acid sequence set forth in SEQ ID NO: 1, a peptide having a sequence homology of 80% or more with the amino acid sequence, or a fragment thereof can be effective in treating and preventing ophthalmopathy.

DETAILED DESCRIPTION OF THE DRAWINGS/FIGURES

DETAILED DESCRIPTION OF THE INVENTION

Best Mode

Figure 1:
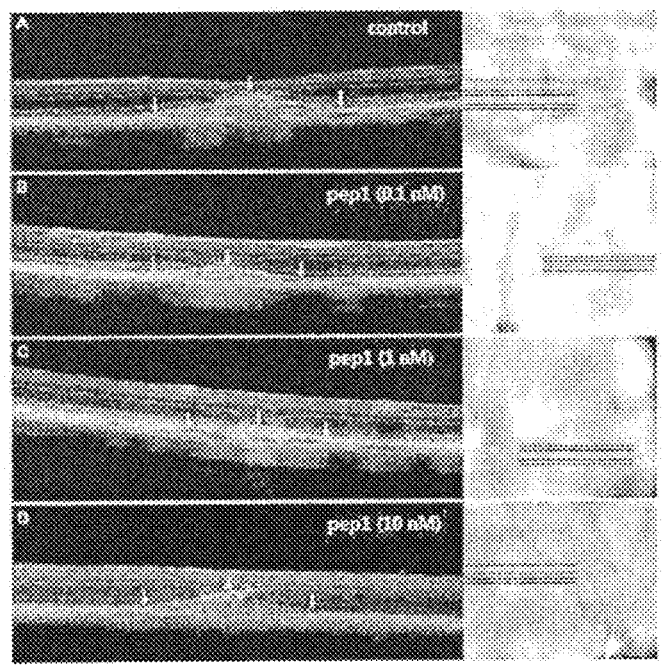
FIG. 1 is an image showing the comparison of thicknesses of choroidal neovascularization (CNV) in experimental groups after pep1 is administered at different concentrations to the experimental groups in a laser-induced CNV animal model.

The present invention can be variously changed and may have various exemplary embodiments. Hereinafter, the present invention will be described in further detail. However, it should be understood that the certain exemplary embodiments proposed herein are not intended to limit the scope of the present invention and cover all such changes and modifications within the scope of the appended claims and their equivalents. In describing the present invention, detailed descriptions of the prior art related to the present invention will be omitted for clarity when the detailed descriptions are considered to obscure the gist of the present invention.

A telomere is a genetic material that is repeatedly located at the end of each chromosome, and is known to prevent damage of the corresponding chromosome or binding to other chromosomes. Whenever cells divide, the length of telomeres is shortened. When not less than a given number of cell division cycles occur, the telomere is extremely shortened, and the cells do not divide any more, which leads to cell death. On the other hand, it is known that the life span of cells is extended when a telomere is lengthened. For example, it is known that cancer cells continue to proliferate without dying because enzymes referred to as "telomerases" are secreted from the cancer cells to prevent the shortening of telomeres. The present inventors have found that peptides derived from the telomerases have an effect in inhibiting the neovascularization. Therefore, the present invention has been completed based on these facts.

The peptide disclosed in this specification may include a peptide having a sequence homology of 80% or more, 85% or more, 90% or more, 95% or more, 96% or more, 97% or more, 98% or more, and 99% or more. Also, the peptide disclosed in this specification may include a peptide containing an amino acid sequence set forth in SEQ ID NO: 1 or fragments thereof, and peptides in which one or more amino acids, two or more amino acids, three or more amino acids, four or more amino acids, five or more amino acids, six or more amino acids, or seven or more amino acids are changed.

According to one aspect of the present invention, the amino acid changes belong to a nature of the peptide to change its physicochemical characteristics. For example, the amino acid changes may be carried out, for example, by improving heat stability of the peptide, altering substrate specificity, changing an optimal pH level, etc.

In this specification, the term "amino acid" includes 22 standard amino acids naturally integrated into peptides and D-isomers thereof, and modified amino acids. Therefore, according to one aspect of the present invention, the peptide may be a peptide including D-amino acids. Meanwhile, according to another aspect of the present invention, the peptide may include non-standard amino acids subjected to post-translational modification, etc. Examples of the post-transnational modification include phosphorylation, glycosylation, acylation (for example, including acetylation, myristoylation, and palmitoylation), alkylation, carboxylation, hydroxylation, glycation, biotinylation, ubiquitinylation, changes in chemical properties (for example, deimidization via β-elimination, deamidation), and structural changes (for example, disulfide bridge formation). Also, the post-translational modification includes changes in amino acids, such as changes in amino acids caused by chemical reactions occurring during the binding to cross-linkers for forming a peptide conjugate, for example, changes in amino groups, carboxyl groups or side chains.

The peptide disclosed in this specification may be a wild-type peptide isolated and separated from a natural source. Meanwhile, the peptide disclosed in this specification may be an artificial variant having an amino acid sequence into which one or more amino acids are substituted, deleted and/or inserted when compared to the peptides that are fragments of the peptide containing an amino acid sequence set forth in SEQ ID NO: 1. The amino acid changes in wild-type polypeptides and artificial variants thereof include conservative amino acid substitution having no significant influence on the folding and/or activities of proteins. Examples of the conservative substitution fall within groups of basic amino acids (arginine, lysine, and histidine), acidic amino acids (glutamic acid and aspartic acid), polar amino acids (glutamine and asparagine), hydrophobic amino acids (leucine, isoleucine, valine, and methionine), aromatic amino acids (phenylalanine, tryptophane, and tyrosine), and small amino acids (glycine, alanine, serine, and threonine). In general the amino acid substitution in which specific activities are not changed is known in the related art. The most generally occurring replacements include Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly replacements, and vice versa. Other examples of the conservation substitutions, are listed in the following Table 1.

TABLE 1

| Original amino acids | Exemplary residue substitution | Preferred residue substitution |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial changes in biological characteristics of the peptide are carried out by selecting substituted sites which have (a) a considerably different effect in maintaining a structure of a polypeptide backbone in a substituted region, for example, a sheet or helical steric confirmation, (b) a considerably different effect in maintaining charges or hydrophobicity of the molecules in a target site, or (c) a considerably different effect in maintaining the bulk of side chains. Natural residues are divided into groups based on the conventional side chain characteristics:

(1) Hydrophobic residues: Norleucine, Met, Ala, Val, Leu, and Ile;
(2) Neutral hydrophilic residues: Cys, Ser, and Thr;
(3) Acidic residues: Asp, and Glu;
(4) Basic residues: Asn, Gln, His, Lys, and Arg;
(5) Residues having an effect on chain orientation: Gly, and Pro; and
(6) Aromatic residues: Trp, Tyr, and Phe.

Non-conservative substitution will be achieved by exchanging one member in these groups with one in another group. Any cysteine residue which is not associated with the maintenance of a proper steric conformation of the peptide may be generally substituted with serine to improve oxidative stability of the molecules and prevent an erroneous cross linked bond. Inversely speaking, a cysteine bond(s) may be added to the peptide to improve the stability of the peptide.

Other types of the amino acid variants of the peptide include amino acid variants in which a glycosylation pattern of an antibody is changed. The term "change" refers to a deletion of one or more carbohydrate residues found in a peptide and (or) an addition of one or more glycosylation sites not present in the peptide.

Typically, the glycosylation of the peptide means that a peptide is N-linked or O-linked. The term "N-linked" means that a carbohydrate residue is attached to a side chain of an asparagine residue. Tripeptide sequences asparagine-X-serine and asparagine-X-threonine (wherein X represents any amino acid other than proline) are recognition sequences for enzymatically attaching a carbohydrate residue to a side chain of asparagine. Therefore, a potential glycosylation site is generated when one of such tripeptide sequences is present in a polypeptide. O-linked glycosylation means that one of sugar N-acetylgalactosamine, galactose and xylose is attached to hydroxyamino acid, most typically serine or threonine. However, 5-hydrozyproline or 5-hydroxylysine may also be used.

The addition of the glycosylation site to the peptide may be easily carried out by modifying an amino acid sequence to including at least one of the aforementioned tripeptide sequences (in the case of N-linked glycosylation sites). Such a change may be carried out by adding one or more serine or threonine residues to an initial sequence of an antibody or substituting these residues (in the case of O-linked glycosylation sites).

Also, the peptide having a sequence set forth its SEQ ID NO: 1 according to one aspect of the present invention, peptides as the fragments of the peptide having a sequence of SEQ ID NO: 1, or peptides having a sequence homology of 80% or more with the peptide sequence has an advantage in that the peptides have low toxicity in cells and high in vivo stability. In the present invention, the peptide having a sequence set forth in SEQ ID NO: 1 is a telomerase-derived peptide that consists of 16 amino acids, as described below.

The peptide having a sequence set forth in SEQ ID NO: 1 is listed in the following Table 2. In the following Table 2, the "name" is used to differentiate peptides from each other. According to one aspect of the present invention, the peptide having a sequence set forth in SEQ ID NO: 1 represents a full-length peptide of a human telomerase. According to another aspect of the present invention, the peptide having a sequence set forth in SEQ ID NO: 1, the peptides as the fragments of the peptide having a sequence of SEQ ID NO: 1, or the peptides having a sequence homology of 80% or more with the peptide sequence includes "synthetic peptides" synthesized after a peptide at a corresponding position is selected from peptides included in the telomerase. SEQ ID NO: 2 represents a full-length amino acid sequence of the telomerase.

TABLE 2

| SEQ ID NO | Name | Location on telomerase | Sequence | Length |
|---|---|---|---|---|
| 1 | pep1 | [611-626] | EARPALLTSRLRFIPK | 16 aa |
| 2 | | [1-1132] | MPRAPRCRAVRSLLRSHYREVLPLATFVRRL GPQGWRLVQRGDPAAFRALVAQCLVCVPW DARPPPAAPSFRQVSCLKELVARVLQRLCER GAKNVLAFGFALLDGARGGPPEAFTTSVRSY LPNTVTDALRGSGAWGLLLRRVGDDVLVHL LARCALFVLVAPSCAYQVCGPPLYQLGAAT QARPPPHASGPRRRLGCERAWNHSVREAGV PLGLPAPGARRRGGSASRSLPLPKRPRRGAAP EPERTPVGQGSWAHPGRTRGPSDRGFCVVSP ARPAEEATSLEGALSGTRHSHPSVGRQHHAG PPSTSRPPRPWDTPCPPVYAETKHFLYSSGDK EQLRPSFLLSSLRPSLTGARRLVETIFLGSRPW MPGTPRRLPRLPQRYWQMRPLFLELLGNHA QCPYGVLLKTHCPLRAAVTPAAGVCAREKP QGSVAAPEEEDTDPRRLVQLLRQHSSPWQV YGFVRACLRRLVPPGLWGSRHNERRFLRNT KKFISLGKHAKLSLQELTWKMSVRDCAWLR RSPGVGCVPAAEHRLREEILAKFLHWLMSVY VVELLRSFFYVTETTFQKNRLFFYRKSVWSK LQSIGIRQHLKRVQLRELSEAEVRQHREARPA LLTSRLRFIPKPDGLRPIVNMDYVVGARTFRR EKRAERLTSRVKALFSVLNYERARRPGLLGA SVLGLDDIHRAWRTFVLRVRAQDPPPELYFV KVDVTGAYDTIPQDRLTEVIASIIKPQNTYCV RRYAVVQKAAHGHVRKAFKSHVSTLTDLQP YMRQFVAHLQETSPLRDAVVIEQSSSLNEAS SGLFDVFLRFMCHHAVRIRGKSYVQCQGIPQ GSILSTLLCSLCYGDMENKLFAGIRRDGLLLR LVDDFLLVTPHLTHAKTFLRTLVRGVPEYGC VVNLRKTVVNFPVEDEALGGTAFVQMPAHG LFPWCGLLLDTRTLEVQSDYSSYARTSIRASL TFNRGFKAGRNMRRKLFGVLRLKCHSLFLDL QVNSLQTVCTNIYKILLLQAAYRFHACVLQLPF HQQVWKNPTFFLRVISDTASLCYSILKAKNA GMSLGAKGAAGPLPSEAVQWLCHQAFLLKL TRHRVTYVPLLGSLRTAQTQLSRKLPGTTLT ALEAAANPALPSDFKTILD | 1,132 aa |

A laser-induced experimental CNV model used in an experiment of the present invention is an animal model which has been most widely used to realize human wet age-related macular degeneration in rats. The rupture of Bruch's membranes may be induced with lasers and neovascularization may grow from the choroid to promote an environment similar to that of the human choroidal neovascularization. Although the human wet age-related macular degeneration caused by chronic, genetic and environmental complex factors, and choroidal neovascularization caused with acute damage with lasers in an animal model cannot be evaluated equally, this animal model plays a critical role as a method of primarily evaluating all age-related macular degeneration therapeutic agents.

In this specification, an experiment is carried out, as follows. In a laser-induced experimental CNV model, pep1 that is a telomerase-derived peptide is administered to determine whether the activities evaluated as a thickness, an area, a leakage level and the like of the choroidal neovascularization are reduced, compared to the control in which a vehicle is administered alone.

According to one aspect of the present invention, a pharmaceutical composition including the peptide as an active ingredient is provided. Here, the peptide is selected from the peptide including an amino acid sequence set forth in SEQ ID NO: 1, the peptides having a sequence homology of 80% or more with the amino acid sequence, or fragments thereof, that is, peptides having a therapeutic effect on ophthalmopathy by reducing a choroidal neovascularization activity.

In one aspect, the composition having a therapeutic effect on ophthalmopathy according to one aspect of the present invention may include the peptide including an amino acid sequence of SEQ ID NO: 1, the peptides having a sequence homology of 80% or more with the amino acid sequence, or the peptides as the fragments thereof at a content of 0.01 g/L to 1 kg/L, particularly 0.1 g/L to 100 g/L, and more particularly 1 g/L to 10 g/L, but the content of the peptide may be properly adjusted when there is a difference in effects according to the content. When the peptide is included within this content range or less, it is desirable for the peptide to have an intended effect of the present invention, and it is possible to satisfy all the stability and safety of the composition. Accordingly, it is desirable that the peptide is included within this content range in terms of cost effectiveness.

The composition according to one aspect of the present invention may be applied to all types of animals including a human, dog, a chicken, a pig, cattle, a sheep, a guinea pig, or a monkey.

According to one aspect of the present invention, the composition is a pharmaceutical composition including the peptide including an amino acid sequence set forth in SEQ ID NO: 1, the peptides having a sequence homology of 80% or more with the amino acid sequence, or fragments thereof, that is, peptides having an inhibitory effect on neovascularization. The pharmaceutical composition according to one aspect of the present invention may be administered orally, intrarectally, percutaneously, intravenously, intramuscularly, intraperitoneally, intramedullarily, intradurally, or subcutaneously.

A formulation for oral administration may include a tablet, a pill, a soft or hard capsule, a granule, a powder, a liquid, or an emulsion, but the present invention is not limited thereto. A formulation for parenteral administration may include an injection, a drop, a lotion, an ointment, a gel, a cream, a suspension, an emulsion, a suppository, a patch, or a spray, but the present invention is not limited thereto.

The pharmaceutical composition according to one aspect of the present invention may include an additive such as a diluent, an excipient, a lubricant, a binding agent, a disintegrating agent, a buffer, a dispersing agent, a surfactant a coloring agent, a flavoring agent, a sweetening agent, etc. when necessary. The pharmaceutical composition according to one aspect of the present invention may be prepared using conventional methods known in the related art.

In the pharmaceutical composition according to one aspect of the present invention, the dose of the active ingredient may vary depending on the age, sex, and weight of a target into which the composition is to be administered, pathological conditions and severity thereof, a route of administration, or the prescriber's judgement. The determination of a proper dose based on these factors is realized within the level of skill of a person of ordinary skill in the art. A daily dose of the composition may, for example, be in a range of 10 ng/kg/day to 10 mg/kg/day, particularly 0.1 μg/kg/day to 1 mg/kg/day, more particularly 1 μg/kg/day to 100 μg/kg/day, and most particularly 2 μg/kg/day to 50 μg/kg/day, but may be properly adjusted when there is a difference in effects according to the content. The pharmaceutical composition according to one aspect of the present invention may be administered once to three times a day, but the present invention is not limited thereto.

According to one aspect of the present invention, the composition is a food composition for inhibiting neovascularization, which includes the peptide including an amino acid sequence set forth in SEQ ID NO: 1, the peptides having a sequence homology of 80% or more with the amino acid sequence, or the peptides serving as the fragments thereof as an active ingredient.

A formulation of the food composition according to one aspect of the present invention is not particularly limited, but may, for example, be prepared into formulations such as a tablet, a granule, a powder, a liquid, a solid preparation, etc. A person having ordinary skill in the art may prepare each of the formulations by properly choosing and admixing components generally used in the related art in addition to the active ingredient, depending on the type of formulations or a purpose of use without any difficulty. In this case, a synergistic effect may be achieved when the components and other materials are applied together.

The terms used in this specification are is intended to be used to described the specific exemplary embodiments, not a limit the present invention. Terms without numbers in front thereof are not to limit the quantity, but to show that there may be more than one thing about the term used. The terms "comprising," "having," "including," and "containing" shall be interpreted as open terms (i.e., "including but not limited to").

The mention of a numerical range is used instead of stating separate numbers within the range, so unless it is explicitly stated, the range should be construed as if all the numbers within the range are separately described herein. The end values of all the ranges are included in the range and can be combined independently.

Unless otherwise noted or clearly contradicting in context, all methods mentioned herein can be performed in a proper order. The use of any one embodiment and all embodiments, or exemplary languages (e.g., "~"), unless included in the claims, is used to more clearly describe the present invention, not to limit the scope of the present invention. Any language herein outside of the claims should not be interpreted to be necessary for the present invention. Unless defined otherwise, technical and scientific terms used herein have the meanings ordinarily understood by a person skilled in the art to which the present invention belongs.

The preferred exemplary embodiments of the present invention include the best mode known to the inventors to practice the present invention. Variations in the preferred embodiments can become clear to those skilled in the art after reading the statements above. The present inventors expect that those skilled in the art can use the variations adequately and the present invention be practiced in other ways than listed herein. Thus, the present invention, as allowable by the patent law, includes equivalents, modifications and variations thereof, of the key points of the invention stated in the appended claims. In addition, all the possible variations within any combination of the above-mentioned components are included in the present invention, unless explicitly stated otherwise or contradicting in context. Although the present invention is described and shown with reference to the exemplary embodiments thereof, those skilled in the art will sufficiently understand that various changes and modifications can be made to the forms and details without departing from the spirit and scope of the prevent invention as defined by the claims below.

Mode for Invention

Hereinafter, the configurations and effects of the present invention will be described in further detail with reference to examples and experimental examples thereof. However, it should be understood that the following examples and experimental examples are merely provided to aid in understanding the present invention, but not intended to limit the scope of the present invention.

Example 1: Synthesis of Peptide

Synthesis of Peptide

A peptide including an amino acid sequence set forth in SEQ ID NO: 1 (hereinafter referred to as "PEP 1") was prepared using a solid-phase peptide synthesis method known in the related art. Specifically, peptides were synthesized by coupling amino acids from the C-termini thereof one by one through Fmoc solid-phase peptide synthesis (SPPS) using ASP48S (Peptron, Inc., Daejeon ROK). The peptides having the first amino acid at the C-terminus attached to a resin were used, as follows:
NH2-Lys(Boc)-2-chloro-Trityl Resin
NH2-Ala-2-chloro-Trityl Resin
NH2-Arg(Pbf)-2-chloro-Trityl Resin All the amino acid sources used to synthesize the peptides were protected by Fmoc at the N-terminus thereof, and the amino acid residues were protected by Trt, Boc, t-butylester (t-Bu), 2,2,4,6,7-pentamethyl dihydro-benzofuran-5-sulfonyl (Pbf), all of which were removed in an acid. Examples of the protected residues were as follows: Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser (tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Try(tBu)-OH, Fmoc-Ahx-OH, Trt-Mercaptoacetic acid.

2-(1H-benzotriazole-1-yl)-1,1,3,3-tetramenthylaminium hexafluorophosphate (HBTU)/N-hydroxybenzotriazole, (HOBt)/4-methylmorpholine (NMM) were used as coupling reagents. Piperidine in 20% DMF was used to remove Fmoc. To separate the synthesized peptides from a resin or remove a protective group from the residues, a cleavage cocktail [trifluoroacetic acid (TFA)/triisopropylsilane (TIS)/ethanedithiol (EDT)/H$_2$O at a ratio of 92.5/2.5/2.5/2.5] was used.

Each of the peptides was synthesized by repeating the following processes: reacting amino acids, to which an amino acid protective group was coupled as starting materials, with a solid-phase scaffold in a state in which the corresponding amino acids were coupled to the scaffold, washing the scaffold with a solvent, and deprotecting the amino acids. The synthesized peptides were released from the resin, purified by HPLC, subjected to mass spectrometry (MS) to check whether the peptides were synthesized, and then freeze-dried.

The peptides used in this example were subjected to high-performance liquid chromatography. As a result, it was revealed that the purity of all the peptides was greater than or equal to 95%.

Specific peptide synthesis process for preparing a peptide PEP 1 was described, as follows.
1) Coupling An amino acid (8 equivalents) protected with an NH$_2$-Lys(Boc)-2-chloro-trityl resin and coupling agents HBTU (8 equivalents)/HOBt (8 equivalents)/NMM (16 equivalents) dissolved in DMF were mixed together, and reacted at room temperature for 2 hours. Thereafter, the resulting reaction mixture was sequentially washed with DMF, MeOH, and DMF.
2) Fmoc deprotection Piperidine in 20% DMF was added, reacted twice at room temperature for 5 minutes, and then sequentially washed with DMF, MeOH, and DMF.
3) As a basic peptide backbone, NH2-E(OtBu)-a-R(Pbf)-P-A-L-L-T(tBu)-S(tBu-R(Pbf)L-R (Pbf)-F-I-P-K(Boc)-2-chloro-trityl resin was prepared by repeating the aforementioned reactions 1) and 2).
4) Cleavage: a cleavage cocktail was added to the synthesized peptide resin to separate the synthesized peptide from the resin.
5) Cooling diethyl ether was added to the resulting mixture, and then centrifuged to precipitate the synthesized peptide.
6) After the peptide was purified by Prep-HPLC, the molecular weight of the peptide was confirmed by LC/MS. Then, the peptide was freeze-dried to be prepared in a powder form.

Example 2: Establishment of CNV Animal Model and Statistical Processing Method

Establishment of Laser-Induced CNV Mouse Model

Brown Norway rats were anesthetized, and pupils of the eyes were dilated using 0.5% phenylephrine (pupillary dilatation). The target rats having the dilated pupils of the eyes were irradiated with a 577 nm laser (577 nm, diode, 10 μm, 0.05 seconds) 6 to 8 times per eye to cause neovascularization in the choroid. Upon laser irradiation, the eyes were covered with a cover glass, and the rupture of Bruch's membranes was confirmed from the fact that bubbles occurred during irradiation with lasers using a slit lamp delivery system.

Classification of Experimental Groups According to Concentration of Administered Pep1

In a laser-induced CNV mouse model, the rats were randomized to experimental groups in which the peptide pep1 prepared by the method disclosed in Example 1 was administered at three doses of 0.01, 1, and 10 nm, and the control (vehicle) in which pep1 was not administered, and a drug was subcutaneously administered to the rats once a day for a period of time starting from the day before 3 days of laser irradiation to 2 weeks after the laser irradiation.
Statistic Processing To compare the CNV activities between various groups, a Kruskal-Wallis test was used. In this case, the comparison between two groups was performed using a Mann-Whitney U test. A p value was considered to be statistically significant when the p value was less than 0.05.

Example 3: Measurement of CNV Thickness after Pep1 Administration

To check an effect on reduction of CNV, an experiment of measuring a CNV thickness was performed.

After CNV was induced with lasers, the rats in the groups in which pep1 was administered and the rats in the control were anesthetized after the elapse of 2 weeks, and then subjected to optical coherence tomography (OCT) to measure the CNV thickness in vivo.

The groups in which pep1 was administered and the control complied with the experimental groups disclosed in Example 2, and the thicknesses of all lesions in each of the groups were measured to check whether there was a difference in CNV thicknesses between the groups.

From the experimental results, it can be seen that the CNV thicknesses were reduced in all the groups in which pep1 was administered, compared to the thickness of the control in which pep1 was not administered after CNV induction (see FIG. 1).

Figure 2:
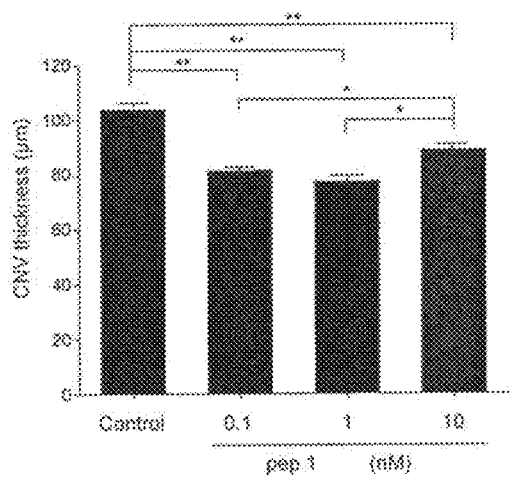
FIG. 2 is a graph plotted for thicknesses of CNV in the experimental groups measured after the pep1 is administered at different concentrations to the experimental groups in a laser-induced CNV animal model.

When the experimental results were plotted on a graph through the statistical processing disclosed in Example 2, it can be seen that the CNV thicknesses were statistically significantly reduced in all the groups in which pep1 was administered at the concentrations (0.1, 1, and 10 nm), compared to the control. In particular, it can be see that the CNV thicknesses were most drastically reduced in the group in which pep1 was administered at a concentration of 1 nm (see FIG. 2).

Example 4: Measurement of CNV Area after Pep1 Administration

To check an effect on reduction of CNV, an experiment of measuring a CNV area was performed.

After CNV was induced with lasers, eyeballs of the rats in the groups in which pep1 was administered and the rats in the control were extracted after the elapse of 2 weeks, and eye lenses and vitreous bodies were removed to obtain retinal pigment epithelium-choroid-sclera tissues. An area of tissues stained with isolectin specific to vascular endothelial cells was measured to determine CNV areas in the control and the groups in which pep1 was administered.

The groups in which pep1 was administered and the control complied with the experimental groups disclosed in Example 2, and the thicknesses of all lesions in each of the groups were measured to check whether there was a difference in CNV areas between the groups.

Figure 3:
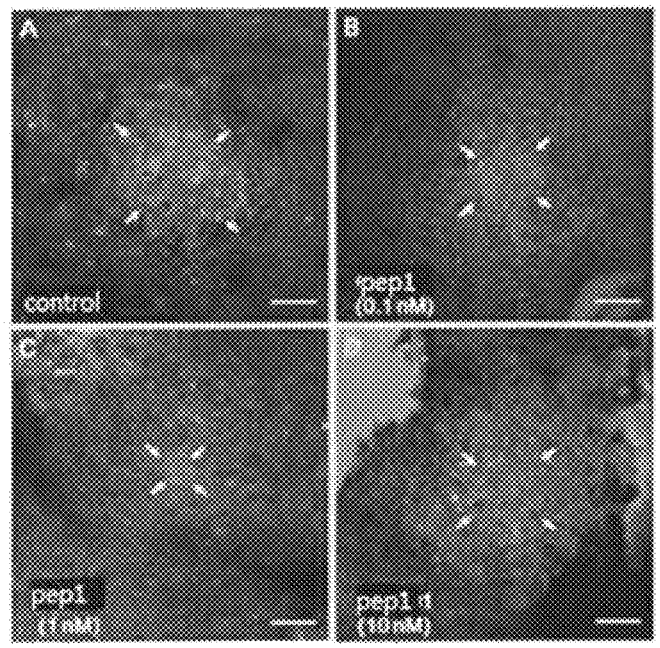
FIG. 3 is an image showing the comparison of areas of choroidal neovascularization (CNV) in experimental groups after pep1 is administered at different concentrations to the experimental groups in a laser-induced CNV animal model.

From the experimental results, it can be seen that the CNV areas were reduced in all the groups in which pep1 was administered, compared to the area of the control in which pep1 was not administered after CNV induction (see FIG. 3).

Figure 4:
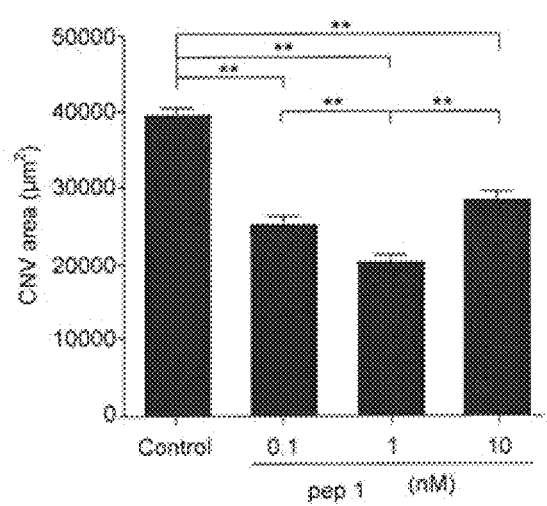
FIG. 4 is a graph plotted for areas of CNV in the experimental groups measured after the pep1 is administered at different concentrations to the experimental groups in a laser-induced CNV animal model.

When the experimental results were plotted on a graph through the statistical processing disclosed in Example 2, it can be seen that the CNV areas were statistically significantly reduced in all the groups in which pep1 was administered at the concentrations (0.1, 1, and 10 nM), compared to the control. In particular, it can be seen that the CNV areas were most drastically reduced in the group in which pep1 was administered at a concentration of 1 nM (see FIG. 4).

Example 5: Measurement of Angiographic Leakage after Pep1 Administration

To check an effect on reduction of CNV, an experiment of measuring angiographic leakage in the choroid was performed.

After CNV was induced with lasers, the rats in the groups in which pep1 was administered and the rats in the control were anesthetized after the elapse of 2 weeks, and a contrast medium was intraperitoneally injected at a dose of 0.1 mL (10% fluorescein disodium salt). Levels of angiographic leakage in the choroid between the control and the groups in which pep1 was administered were compared using fluorescein angiography (FAG).

The groups in which pep1 was administered and the control complied with the experimental groups disclosed in Example 2, and the leakage levels at all lesions in each of the groups were measured to check whether there was a difference in angiographic leakage in the choroid between the groups.

Figure 5:
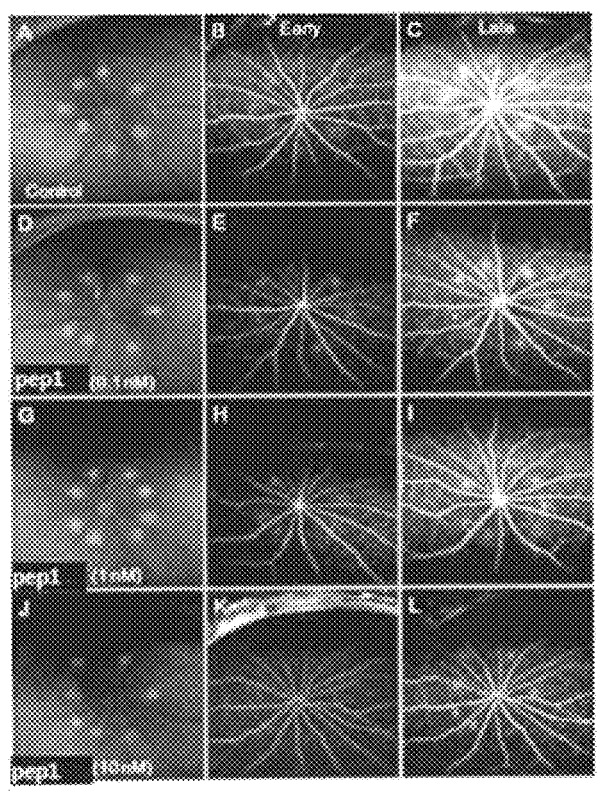
FIG. 5 is an image showing the comparison of levels of angiographic leakage in the experimental groups photographed using fluorescein angiography after the pep1 is administered at different concentrations the experimental groups in a laser-induced CNV animal model.

From the experimental results, it can be seen that the leakage levels were reduced in all the groups in which pep1 was administered at the concentrations (0,1, 1, and 10 nm), compared to the leakage level of the control in which pep1 was not administered after CNV induction (see FIG. 5).

Figure 6:
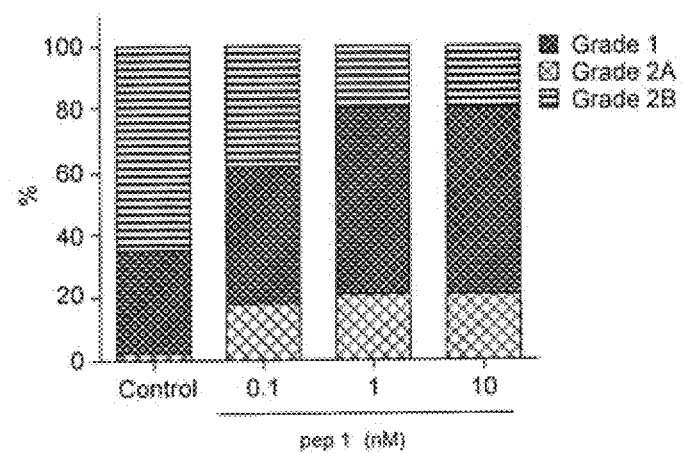
FIG. 6 is a graph plotted for ratios of lesions in the experimental groups evaluated in grades, each of which represents a level of angiographic leakage, alter the pep1 is administered at different concentrations to the experimental groups in a laser-induced CNV animal model.

All the lesions in each of the groups were graded according to the leakage levels, and the ratios of the lesions with respect to the grades in each of the groups were plotted on a graph (see FIG. 6). The grades were indicated as follows: Grade 1 (a clinically mild leakage level), Grade 2A (a clinically mean leakage level), and Grade 2B (a clinically severe leakage level). It was confirmed that the ratios of the lesions with Grade 2B in which the leakage level was severe were reduced in all the groups in which pep1 was administered at the concentrations, compared to the ratios of the control. In particular, it can be seen that the ratios of the Grade 2B lesions were drastically reduced when pep1 was administered at concentrations of 1 and 10 nM.

When the results of Examples 1 to 5 were combined, the three CNV activities including the CNV thickness, the CNV area and the ratio of lesions according to the level of angiographic leakage were measured. As a result, it was revealed that the CNV activities were reduced when pep1 was administered. That is, it was proven that pep1 was effective in treating and preventing CNV-associated ocular diseases by reducing the CNV activities. Therefore, it can be seen that the composition including pep1 was probably used as the pharmaceutical composition for treating and preventing ocular diseases so as to treat and prevent the ocular diseases.

What is claimed is:

1. A method of treating ophthalmopathy, comprising: administering to a subject in need thereof an effective amount of an isolated peptide consisting of the amino acid sequence of SEQ ID NO: 1 for treatment of ophthalmopathy.

2. The method of claim 1, wherein the ophthalmopathy comprises one or more selected from the group consisting of diabetic retinopathy, retinopathy of prematurity, corneal graft rejection, neovascular glaucoma, rubeosis, proliferative retinopathy, dry eye syndrome, and macular degeneration.

3. The method of claim 1, wherein the ophthalmopathy is age-related ophthalmopathy or is caused by choroidal neovascularization.

4. The method of claim 1, wherein the peptide is administered at a daily dose of 10 ng/kg to 10 mg/kg.

5. The method of claim 1, wherein the peptide is administered 1 to 3 times a day.

6. A kit for treating ophthalmopathy, comprising a composition which comprises the isolated peptide of SEQ ID NO: 1; and a manual.

7. A method of treating ophthalmopathy, comprising: administering to a subject in need thereof a composition comprising an effective amount of an isolated peptide consisting of the amino acid sequence of SEQ ID NO: 1 for treatment of ophthalmopathy.

8. The method of claim 7, wherein the ophthalmopathy comprises one or more selected from the group consisting of diabetic retinopathy, retinopathy of prematurity, corneal graft rejection, neovascular glaucoma, rubeosis, proliferative retinopathy, dry eye syndrome, and macular degeneration.

9. The method of claim 7, wherein the ophthalmopathy is age-related ophthalmopathy.

10. The method of claim 7, wherein the ophthalmopathy is caused by choroidal neovascularization.

11. The method of claim 7, wherein the composition comprises 0.01 g/L to 1 kg/L of the peptide.

12. The method of claim 7, wherein the peptide is administered at a daily dose of 10 ng/kg to 10 mg/kg.

13. The method of claim 7, wherein the peptide is administered 1 to 3 times a day.

14. The method of claim 7, wherein the composition is a pharmaceutical composition further comprising a pharmaceutically acceptable excipient and an additive.

15. The method of claim 7, wherein the composition is a food composition.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
```

```
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400
```

```
Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
                515                 520                 525

Val Pro Ala Ala Glu His Arg Leu Arg Glu Glu Ile Leu Ala Lys Phe
        530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
                595                 600                 605

His Arg Glu Ala Arg Pro Ala Leu Leu Thr Ser Arg Leu Arg Phe Ile
        610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
        690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
            805                 810                 815
```

-continued

```
Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
        930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
                980                 985                 990

Ser Leu Gln Thr Val Cys Thr Asn Ile Tyr Lys Ile Leu  Leu Leu Gln
            995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130
```